US010813785B2

(12) United States Patent
Sudell (10) Patent No.: US 10,813,785 B2
(45) Date of Patent: *Oct. 27, 2020

(54) PORTABLE TRACTION DEVICE WITH SLING

(71) Applicant: Steven Sudell, Santa Monica, CA (US)

(72) Inventor: Steven Sudell, Santa Monica, CA (US)

(73) Assignee: The Neck Hammock, Inc., Wilmington, DE (US)

( * ) Notice: Subject to any disclaimer, the term of this patent is extended or adjusted under 35 U.S.C. 154(b) by 665 days.

This patent is subject to a terminal disclaimer.

(21) Appl. No.: 15/600,901

(22) Filed: May 22, 2017

(65) Prior Publication Data

US 2018/0042757 A1   Feb. 15, 2018

Related U.S. Application Data

(60) Provisional application No. 62/374,259, filed on Aug. 12, 2016.

(51) Int. Cl.
| A61F 5/00 | (2006.01) |
| A61F 5/055 | (2006.01) |
| A61F 5/042 | (2006.01) |
| A61H 1/02 | (2006.01) |
| A61F 5/048 | (2006.01) |

(52) U.S. Cl.
CPC .............. *A61F 5/055* (2013.01); *A61F 5/042* (2013.01); *A61H 1/0218* (2013.01); *A61F 5/048* (2013.01); *A61H 2201/0123* (2013.01); *A61H 2201/1611* (2013.01)

(58) Field of Classification Search
CPC ...... A61F 5/055; A61F 5/042; A61H 2205/04

USPC ........................................................ D24/190
See application file for complete search history.

(56) References Cited

U.S. PATENT DOCUMENTS

| 2,674,996 A * | 4/1954 | Stowell ................ A61H 1/0218 |
| | | 602/36 |
| 3,118,443 A | 1/1962 | Dykinga |
| 3,033,198 A | 5/1962 | Jensen |
| 3,221,735 A | 12/1965 | Manoah |
| D213,478 S | 3/1969 | Nightingale |
| 4,220,147 A | 9/1980 | Allen, III |
| D332,495 S | 1/1993 | Lake |
| 5,451,202 A | 9/1995 | Miller et al. |
| 5,479,667 A | 1/1996 | Nelson et al. |
| D422,710 S | 4/2000 | Maynard |

(Continued)

FOREIGN PATENT DOCUMENTS

GB    1315519    12/1970

OTHER PUBLICATIONS

Selenechen Hammock for Neck, Neck Massager for Men Women, Relaxation Massager Great for Neck Pain Relief Amazon.

(Continued)

*Primary Examiner* — Kim M Lewis
(74) *Attorney, Agent, or Firm* — Workman Nydegger (57) ABSTRACT

A sling of a portable traction device cradles a user's head primarily at the back and lower part of the skull. The sling is attached to at least one shock cord. The at least one shock cords is also anchored to a structure, such as a closed door at the hinged side of the door, between the door and door frame, using an anchor, at a height, to generate a tension vector at an acute angle relative to the floor. The tension applies cervical traction.

19 Claims, 11 Drawing Sheets

(56) References Cited

U.S. PATENT DOCUMENTS

| | | |
|---|---|---|
| 6,113,564 A | 9/2000 | McGuire |
| 6,183,501 B1 | 2/2001 | Latham |
| 6,939,269 B2 | 9/2005 | Makofsky |
| D550,847 S | 9/2007 | Kixmiller |
| D626,244 S | 10/2010 | Sagnip |
| 8,657,774 B1 * | 2/2014 | Fisher .................. A61H 1/0292 602/32 |
| 8,782,831 B2 | 7/2014 | Houston |
| D713,049 S | 9/2014 | Shah |
| D713,535 S | 9/2014 | Chiang et al. |
| D749,230 S | 2/2016 | Safko |
| 9,526,965 B2 * | 12/2016 | Gatherer ............ A63B 71/0054 |
| D784,546 S | 4/2017 | Gordon |
| D789,546 S | 6/2017 | Matfus |
| D790,072 S | 6/2017 | Hiebert |
| 9,668,906 B2 | 6/2017 | Thorsteindottir |
| 9,713,546 B2 | 7/2017 | Thorsteindottir |
| D794,809 S | 8/2017 | Gramza |
| D812,236 S | 3/2018 | Burke |
| 10,307,284 B2 * | 6/2019 | Sudell .................. A61H 1/0218 |
| 2005/0113728 A1 * | 5/2005 | Heinz ..................... A61F 5/055 602/18 |
| 2006/0288490 A1 | 12/2006 | Mikkelsen et al. |
| 2010/0222729 A1 | 9/2010 | Chin et al. |
| 2014/0249461 A1 * | 9/2014 | Bissell ................. A61H 1/0218 602/36 |
| 2018/0028389 A1 * | 2/2018 | Adimari ............... A61H 1/0292 |
| 2018/0161192 A1 | 6/2018 | Sudell |

OTHER PUBLICATIONS

U.S. Appl. No. 29/640,156, Apr. 12, 2018, Office Action.
International Search Report and Written Opinion issued in PCT/US2018/015415 dated Mar. 22, 2018.
Notice of Allowance issued in U.S. Appl. No. 16/008,247 dated Feb. 1, 2019.
Office Action issued in U.S. Appl. No. 16/008,247 dated Sep. 20, 2018.

* cited by examiner

PORTABLE TRACTION DEVICE WITH SLING

RELATED APPLICATION

This application is a Nonprovisional of and claims the benefit of priority of U.S. Provisional Application 62/374,259 filed Aug. 12, 2016.

FIELD OF THE INVENTION

This invention relates generally to cervical traction, and, more particularly, to a portable device to apply cervical traction.

BACKGROUND

Cervical traction is a method of applying force to relieve neck pain for individuals suffering from neck arthritis, a herniated/bulging disc in the neck, pinched nerves, neck strains and cervical muscle spasms. Cervical traction entails urging the head away from the neck. Doing so, gradually stretches muscles and ligaments around the vertebrae of the spine and expands space between vertebrae. Pinched nerves are released. Herniated and bulging discs relax as pressure is relieved. Blood circulation improves to the structures of the cervical spine, helping to oxygenate muscles, nerves, tendons and ligaments.

In the past, individuals were relegated to visiting a physical therapist for neck traction. Such visits are time consuming, often inconvenient and costly. Additionally, patients can afford such visits only periodically.

Today, home cervical traction devices are legion. Using such a device, an individual apply traction effectively, conveniently and frequently. Unfortunately, however, many of the devices are complex, cumbersome, bulky, costly and potentially injurious.

As one example, many home traction devices include headgear which include straps around the user's forehead head and chin. Such headgear is not only cumbersome, constricting and inconvenient, but may also exert stresses at the jaw that may lead to or exacerbate temporomandibular disorders. As another example, many such devices require weights and pulleys to exert tension. Such devices are bulky, cumbersome and inconvenient. As yet another example, many devices include clamps and brackets for attachment to doors and furniture. Such hardware mars surface finishes and interferes with use of the door or furniture.

What is needed is an easy to use, compact, non-marring, effective traction device that minimizes discomfort and avoids potentially injurious stresses.

The invention is directed to overcoming one or more of the problems and solving one or more of the needs as set forth above.

SUMMARY OF THE INVENTION

To solve one or more of the problems set forth above, in an exemplary implementation of the invention, a portable traction device according to principles of the invention includes a sling. The sling is elongated and has a first side, a second side opposite the first side, a superior edge and an inferior edge. The sling is made of a flexible material. The sling is sized to cradle an occipital bone portion of a user's head between the superior edge and the inferior edge of the sling, while the first side extends to a first side of the user's head and the second side extends to a second side of the user's head. A frictional portion of the sling frictionally engages the occipital bone portion of the user's head. A pair of side attachments, including a first side attachment and a second side attachment, extend from the first side of the sling, and the second side attachment extending from the second side of the sling. Each of a pair of flexible elastic tethers (e.g., shock cords) includes a proximal end and a distal end. The proximal end of a first tether is attached to the first side attachment of the sling and the proximal end of the second tether attached to the second side attachment of the sling. An anchor is removably attached to an anchoring object, at a height above a floor, while the portable traction device is in use. The distal end of each of the pair of flexible elastic tethers is attached to the anchor. During use, the flexible elastic tethers are strained and at an acute angle relative to the floor. The strained flexible elastic tethers producing a tensile force that includes a vector component parallel to the floor towards the anchor, and a vector component perpendicular to the floor and upward. The superior edge of the sling is arcuate. At least one cushion is provided on the sling between the superior edge and the inferior edge, with one cushion being approximately centered between the first side of the sling and the second side of the sling, and two cushions flanking the centered cushion. Optionally, the sling includes a first layer, a second layer and a third layer, with the first layer and the third layer being flexible fabric, and the second layer being disposed between the first layer and the third layer and being a cushioning material. The exemplary sling includes a back side and a front side opposite the back side. The front side of the sling contacts a user's head when in use. A strap extends from the first side attachment across the back side of the sling to the second side attachment, beyond the first side of the sling and the second side of the sling, and attached to the back side of the sling. Each of the pair of side attachments may be a shackle, ring, hook or clip. Each of the pair of flexible elastic tethers may be a shock cord. The proximal end of each of the pair of flexible elastic tethers includes a first connector, and the distal end of each of the pair of flexible elastic tethers including a second connector, with each such connector being a hook, carabiner or shackle. The anchor includes an anchor tab, an anchor strap and an anchor connector. The anchor strap is between and connects the anchor tab and the anchor connector. The anchor connector is attached to each distal end of each of the pair of flexible elastic tethers.

A method of applying cervical traction to a user using the exemplary portable traction device includes steps of attaching the anchor to the anchoring object, at a height above the floor; stretching the pair of flexible elastic tethers at an acute angle relative to the floor to produce a tensile force including a vector component parallel to the floor towards the anchor, and a vector component perpendicular to the floor and upward; and cradling, with the sling, while the pair of flexible elastic tethers is stretched, the head of the user, the user being substantially supine on a floor, with the user's head spaced apart from and aimed towards the anchoring object, and the user's feet aimed away from the anchoring object. The height above the floor is about at least two feet. The tensile force is at least five pounds.

A portable traction device according to principles of the invention thus provides an easy to use, compact, portable, stowable, non-marring, effective traction device that minimizes discomfort and avoids potentially injurious stresses.

BRIEF DESCRIPTION OF THE DRAWINGS

The foregoing and other aspects, objects, features and advantages of the invention will become better understood with reference to the following description, appended claims, and accompanying drawings, where:

Those skilled in the art will appreciate that the figures are not intended to be drawn to any particular scale; nor are the figures intended to illustrate every embodiment of the invention. The invention is not limited to the exemplary embodiments depicted in the figures or the specific components, configurations, shapes, relative sizes, ornamental aspects or proportions as shown in the figures.

DETAILED DESCRIPTION

A portable traction device according to principles of the invention provides an easy to use, compact, non-marring, effective traction device that minimizes discomfort and avoids potentially injurious stresses. A sling cradles a user's head, particularly the occipital bone portion of the user's head situated at the back and lower part of the skull. The sling includes cushions for comfort and enhanced frictional engagement of the user's head. The sling also includes an arched portion that extends beyond the occipital bone portion of the user's head to the lambdoid suture and lateral portion of the parietal bones of the user's head. The sling is attached to one end of each of a pair of shock cords. The other end of each of the pair of shock cords is anchored to a fixed or immovable object (i.e., an anchoring object) such as a closed door at the hinged side of the door, between the door and door frame, using a door anchor. The door anchor is positioned at a height near the middle of the door. Tension exerted by the shock cords is directed from the cradled portion of the user's head to the anchor, at an acute angle relative to a horizontal floor surface. Thus the tensile force vector includes a horizontal component away from the user's head towards the door, and a vertical component upwardly from the floor. The upward component helps to ensure that the sling does not slip off and disengage the user's head. The invention is not limited to attachment to a door. Other elevated structures such as furniture, including table legs, may be used for anchoring.

Figure 1:
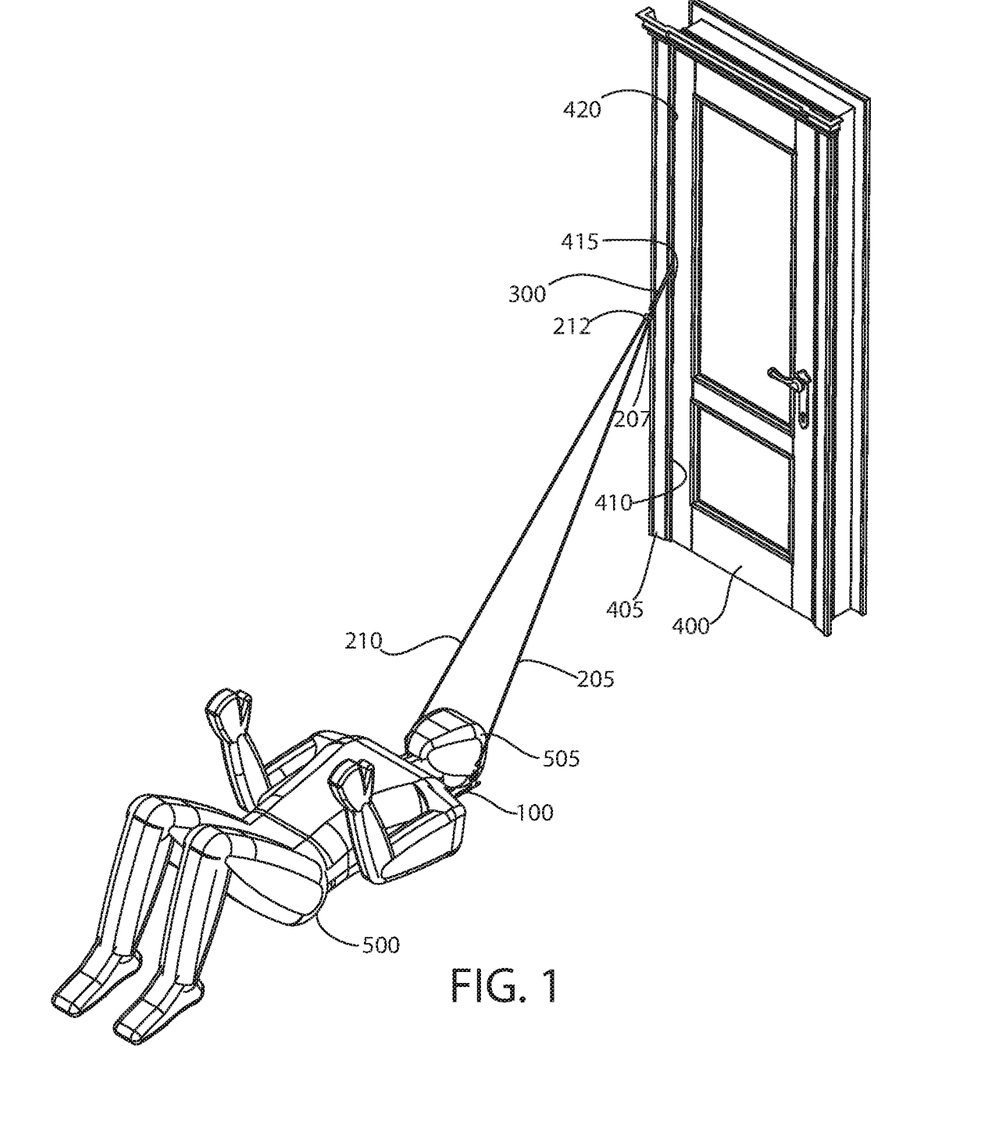
FIG. 1 is a top perspective view that conceptually illustrates a traction device in use according to principles of the invention.
Figure 2:
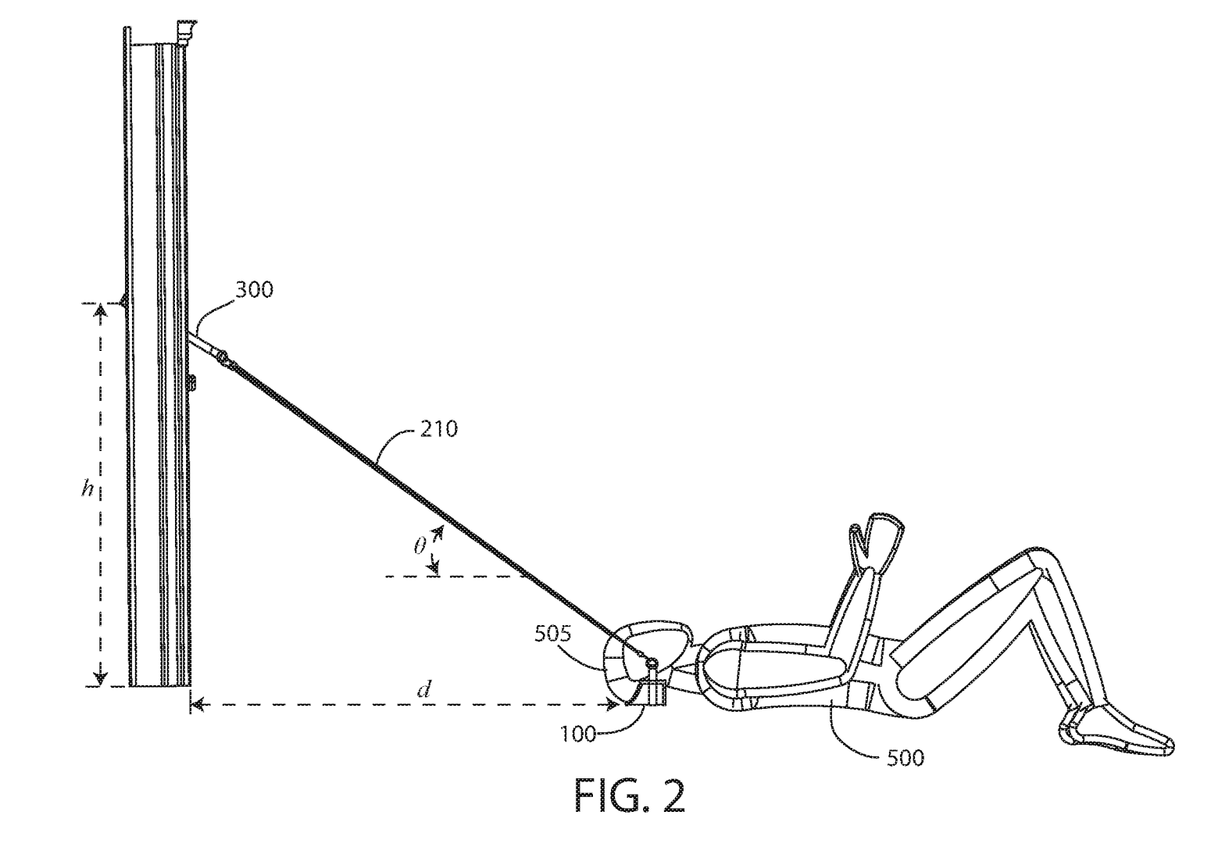
FIG. 2 is a side view that conceptually illustrates a traction device in use according to principles of the invention.
Figure 3:
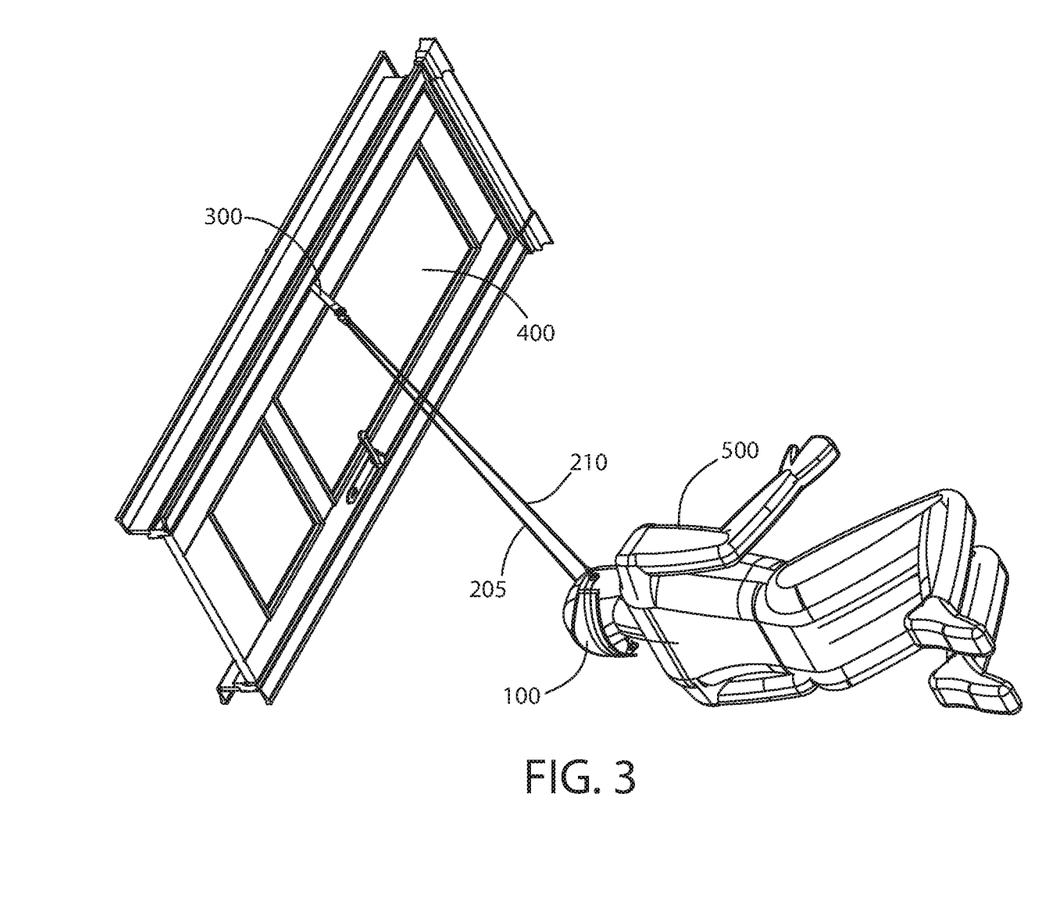
FIG. 3 is a bottom perspective view that conceptually illustrates a traction device in use according to principles of the invention.

Referring to FIGS. 1 through 3 a traction device in use according to principles of the invention is conceptually illustrated. A sling assembly 100, which is described in greater detail below with reference to FIGS. 4 and 5, cradles a user's 500 head 505, particularly the occipital bone portion of the user's head situated at the back and lower part of the skull. The sling assembly 100 extends beyond the occipital bone portion of the user's head to the lambdoid suture and lateral portion of the parietal bones of the user's head. Each of a plurality (e.g., an even number) of shock cords 205, 210 is attached at one end to the sling assembly, and at the opposite end 207, 212 to a door anchor 300, where the ends 207, 212 converge. The door anchor 300 is described in greater detail below with reference to FIGS. 7 through 9. The door anchor 300 is locked between the hinged edge of the door 400 and the door frame 405, when the door 400 is closed. In such an embodiment, the closed door is deemed an anchoring object while the sling assembly 100 is in use.

With reference to FIG. 2, net tension exerted by the shock cords 205, 210 is directed from the cradled portion of the user's head 505 to the anchor 300, at an acute angle θ (greater than 0° but less than 90°, preferably between 15° and 60°) relative to a planar (e.g., horizontal floor) surface. Thus the tensile force vector includes a horizontal component away from the user's head 505 towards the door 400, and a vertical component upwardly from the floor. The vertical component helps to ensure that the sling 100 does not slip off and disengage the user's head 505. The vertical component of the tensile force and friction between the user's head and the sling assembly 100 obviate need for a chin strap or other cumbersome head attachment. A portion of the sling 100 that cradles the user's head, particularly at the occipital bone portion of the user's head situated at the back and lower part of the skull, is a frictionally engaging portion that does not slide off the head during normal use. During normal use, the sling assembly 100 will not slide out from beneath the user's head 505. The angle θ and horizontal and vertical components of the force vector may be varied by adjusting d, the distance from the door, and h, the height of the anchor.

While the Figures may illustrate the user's head against (or nearly against) the floor, it is understood that the vertical component of the tensile force may pull the user's head upward from the floor. Such lifting of the user's head 505 provides considerable comfort to the user without appreciably compromising the horizontal component of the tensile force. A user may counteract the lifting force by urging his or her head against the floor. However, such counteraction is unnecessary.

In the bottom-up perspective view of FIG. 3, the sling assembly 100 relative to the head 505 is more clearly illustrated. The sling assembly 100 cradles the user's 500 head 505, particularly the occipital bone portion of the user's head situated at the back and lower part of the skull. The sling assembly 100 extends beyond the occipital bone portion of the user's head to the lambdoid suture and lateral portion of the parietal bones of the user's head.

Figure 10:
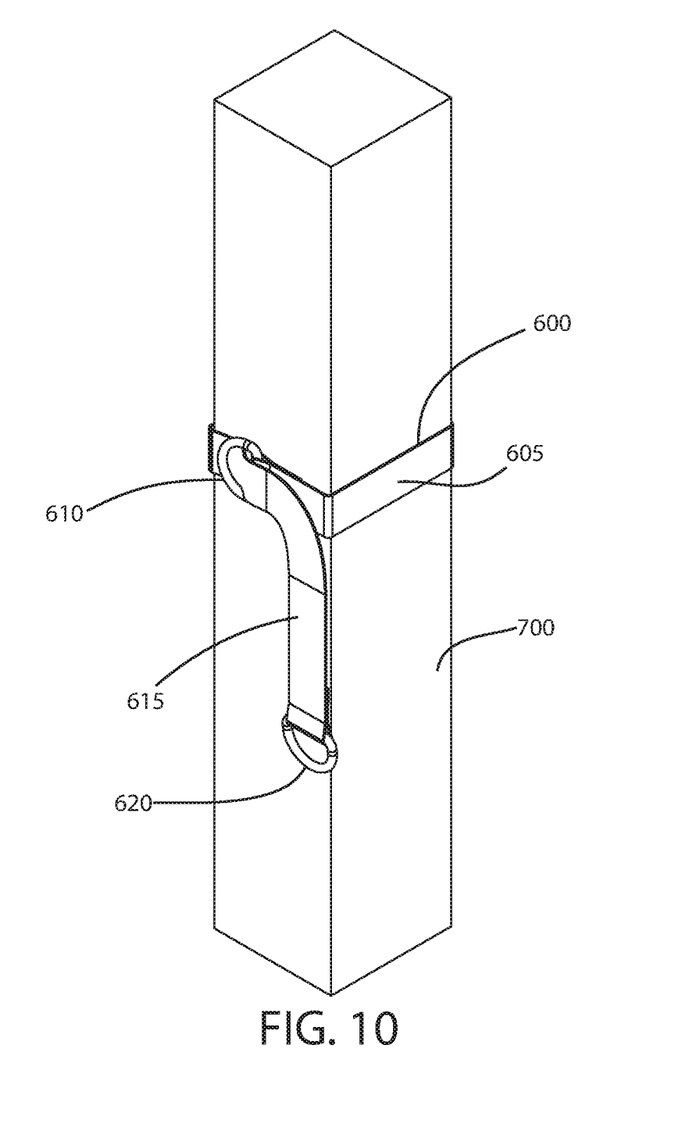
FIG. 10 is a top perspective view of a leg anchor, in use, for a traction device according to principles of the invention.

While the illustrated door 400 includes three hinges 410, 415, 420 with the anchor 300 above the intermediate hinge 415, the invention is not limited to such a configuration. Rather, the invention may be used with doors having fewer or more hinges. Even without an intermediate hinge 415, the anchor 300 may be frictionally secured (i.e., clamped) between the door 400 and frame 405 at a height above the bottom of the door. Structures other than a door may be used for anchoring in accordance with principles of the invention, as discussed in more detail below with reference to FIG. 10.

Figure 4:
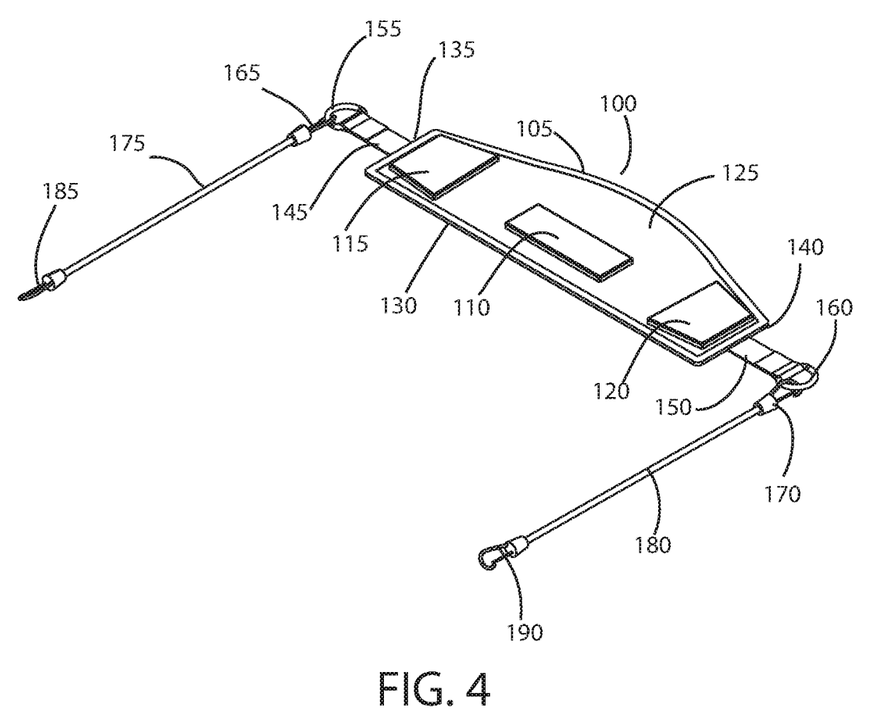
FIG. 4 is a top perspective view that conceptually illustrates a sling assembly for a traction device in use according to principles of the invention.
Figure 5:
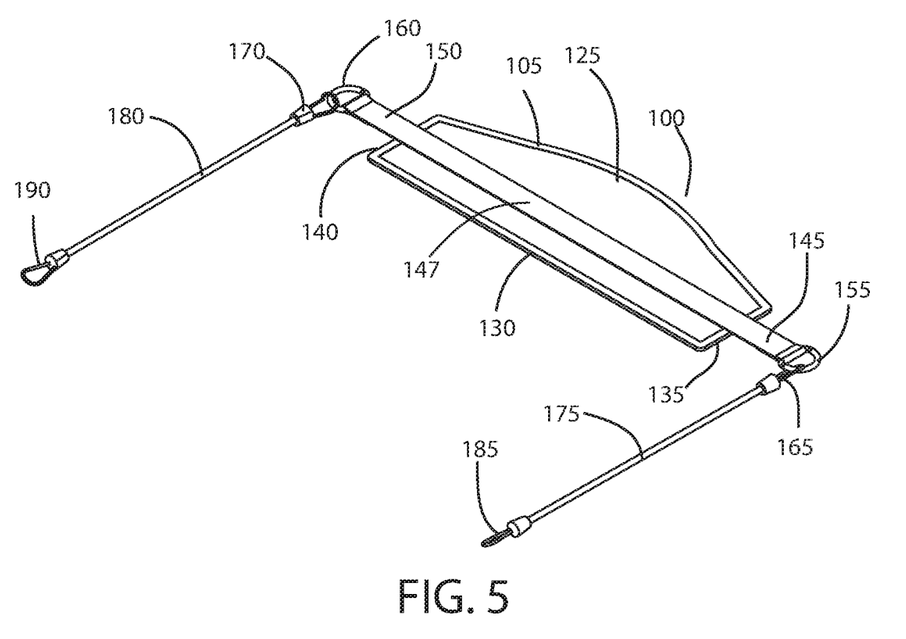
FIG. 5 is a bottom perspective view that conceptually illustrates a sling assembly for a traction device in use according to principles of the invention.

Referring now to FIGS. 4 and 5, the sling assembly 100 and shock cords 205, 210 are more clearly shown. Each shock cord 205, 210 includes an elastic cord 175, 180 composed of one or more elastic strands forming a core, covered in a woven sheath. While the sheath does not extend elastically, its strands spiral around the core so that a longitudinal pull causes it to squeeze the core, transmitting the core's elastic compression to the longitudinal extension of the sheath and cord. Elastic cords other than sheathed shock cords may be utilized without departing from the scope of the invention. Non limiting examples include elastic straps such as EPDM and natural rubber tarp straps equipped with S-hooks at each end.

The shock cords 205, 210 or other elastic cords exert a tension when stretched. The tensile force is preferably at least 5 lbs for cervical traction, more preferably 10 to 30 pounds, and up to 5% to 10% of the user's body weight. A plurality of (e.g., 2, 4, 6 or 8) shock cords may be used to achieve a desired tensile force. Additionally, tension is a function of the strain (i.e., ΔL/L, where L is the original length and ΔL is the elongation) of the shock cord or elastic cord, with tension increasing with increasing strain. Thus, tensile force may be adjusted by adjusting the strain.

Each shock cord 205, 210 includes a metal or plastic hook 165, 185 and 170, 190 attached to each end of the cord 205, 210. The hooks 165, 185 and 170, 190, may be opened or closed. Attachments other than hooks, such as shackles, carabiners and straps may be utilized, at either or both ends of each shock cord to guard against unintentional disengagement of the shock cord.

A strap 147 disposed across the base 125 of the sling assembly includes ends 145, 150 that extend away from opposite side edges 135, 140 of the sling assembly. A nonlimiting example of a suitable flexible strap is nylon webbing. Attachments, such as D-rings 155, 160 are attached to the free ends of the strap ends 145, 150. Shock cords 205, 210 connect to the attachments, i.e., to the D-rings 155, 160. As shown in FIG. 5, the strap ends 145, 150 may be opposite ends of strap 147 that extends across the bottom of sling assembly 100. The strap 147 may be permanently or removably attached to the sling assembly, such as with stitching, hook and loop fasteners, or belt loops.

The base 125 of the sling assembly 100 includes a top edge 105 with an arched (convex) section, an opposite bottom edge 130, and opposite side edges 135, 140. The base 125 is substantially planar. It may be comprised of any flexible fabric, including natural or synthetic fiber fabrics, that is comfortable, strong and durable. Nylon webbing, ballistic nylon fabric, nylon pack cloth, nylon canvass are non-limiting examples.

A plurality of cushions 110, 115, and 120 are provided for comfort at all pressure points. While three cushions are illustrated, one large cushion or several separate cushions may be used. Base cushion 110 is positioned where the occipital bone portion of the user's head will be located during normal use. Side cushions 115, 120 are positioned to cushion the sides of a user's head, below the ears, where the lambdoid suture and lateral portions of the parietal bones of the user's head are located.

Figure 6:
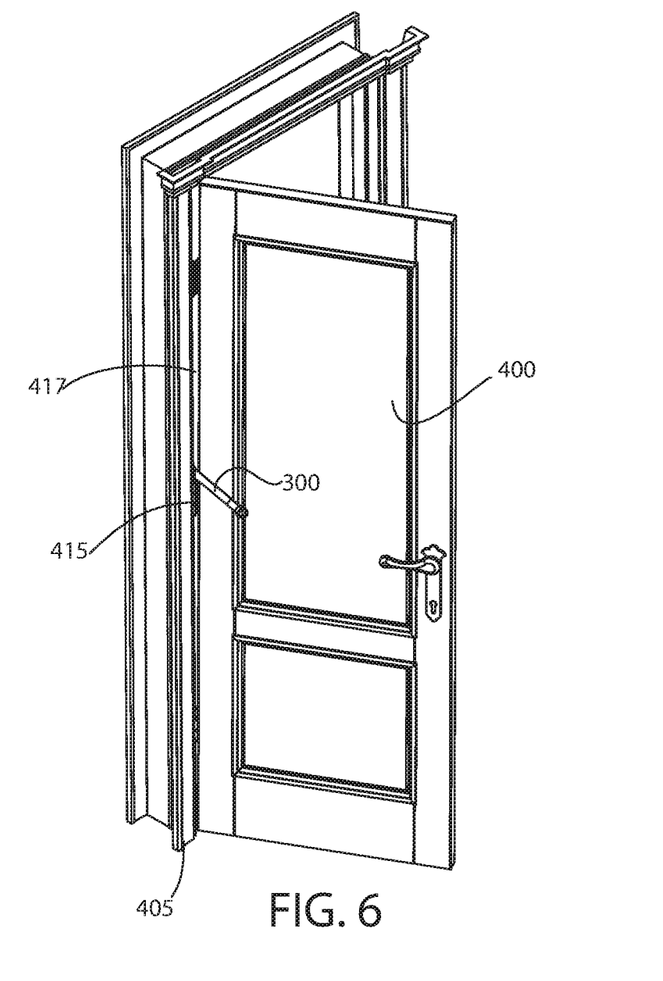
FIG. 6 is a top perspective view that conceptually illustrates a door anchor, in use, for a traction device according to principles of the invention.

In an exemplary implementation, an anchor is attached to a door 400, actually between the hinged side of the door 400 and the door frame 405. When the door is opened as shown in FIG. 6, an anchor tab 315 of an anchor 300 is slipped through the space 417 exposed between the hinged edge of the door 400 and the door frame 405, at a desired height. When the door 400 is closed, the space 417 is reduced or eliminated to prevent dislodging the anchor tab 315.

Figure 7:
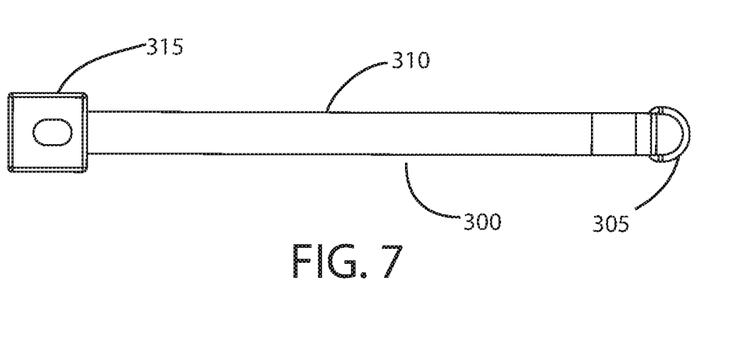
FIG. 7 is a plan view of a door anchor for a traction device according to principles of the invention.
Figure 8:
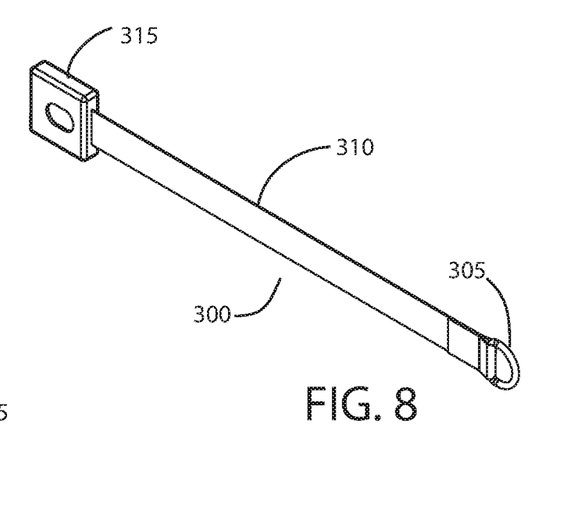
FIG. 8 is a top perspective view of a door anchor for a traction device according to principles of the invention.
Figure 9:
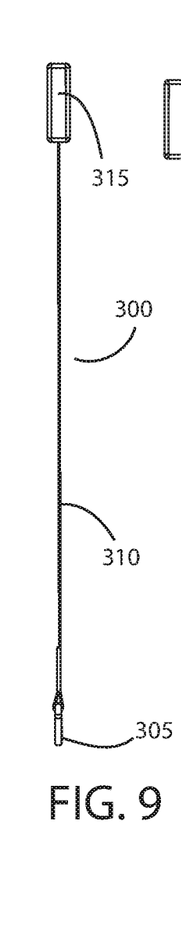
FIG. 9 is a side view of a door anchor for a traction device according to principles of the invention.

With reference to FIGS. 7 through 9 an exemplary door anchor 300 for a traction device according to principles of the invention is conceptually illustrated. The anchor includes a flexible strap 310 (e.g., nylon webbing) with an attachment (e.g., D-ring) 305 at one end, and an anchor tab 315 at the opposite end. The anchor tab 315 is sized to fit through the space exposed between the hinged edge of a door and a door frame, when the door is open. However, the anchor is thick enough to resist withdrawal through the space when the door is closed. The anchor tab 315 is firmly attached to the end of the strap 310 to prevent disconnection. The anchor tab may comprise a plastic tab of 0.1 to 0.5 inches in thickness, or folded and sewn lawyers of webbing with stitched seams, or other rigid structures including hardwood, metal and composite prismatic polyhedron shaped tab-like structures of appropriate size. The strap 310 is thin enough to allow closure of the door with the strap 310 between the hinged edge and frame of the door. While a D-ring 305 is illustrated for attachment to shock cord 205, 210, other attachments such as carabiners, shackles, loops, spring clips, buckles and the like may be utilized within the scope of the invention.

Attachment to a door is preferred, as doors are ubiquitous. However, an anchor may be attached to other structures such as a table leg 700 as conceptually illustrated in FIG. 10. In this embodiment, the anchor 600 is comprised of a strap 605 with D-rings 610, 620 at each end, and a segment of the strap 615 threaded through one of the D-rings 610 to define a slip knot or noose surrounding the periphery of the leg 700 at a certain height. In such an implementation, one D-ring 610 may also serve as an anchor tab for use with a door.

Figures 11, 12:
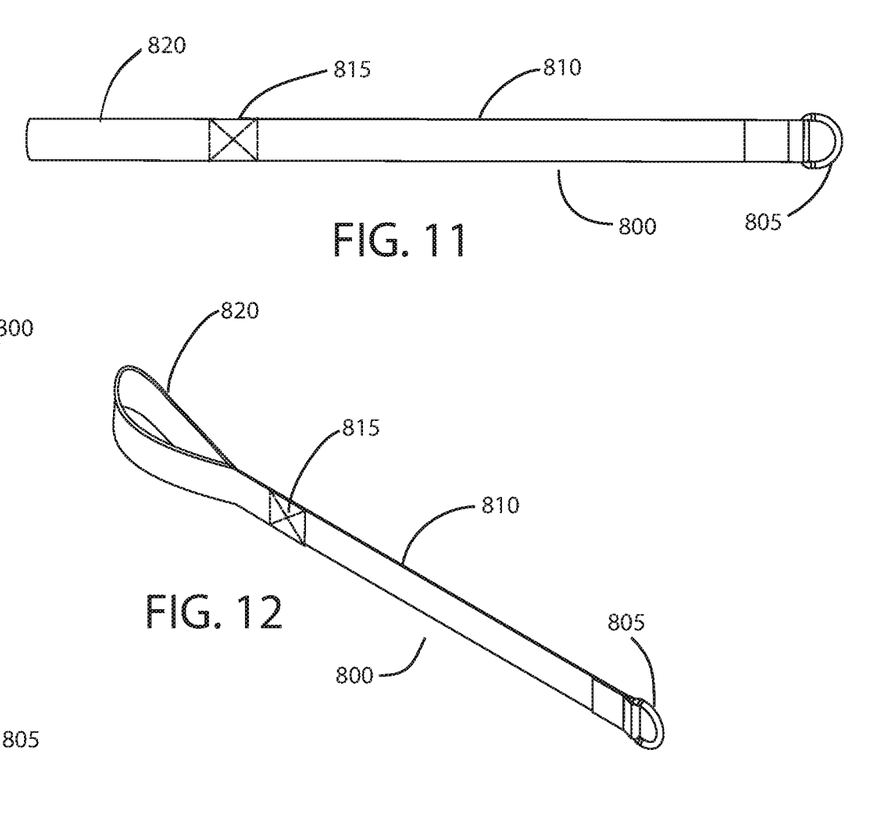
FIG. 11 is a plan view of a door anchor for a traction device according to principles of the invention.
FIG. 12 is a top perspective view of a door anchor for a traction device according to principles of the invention.
Figure 13:
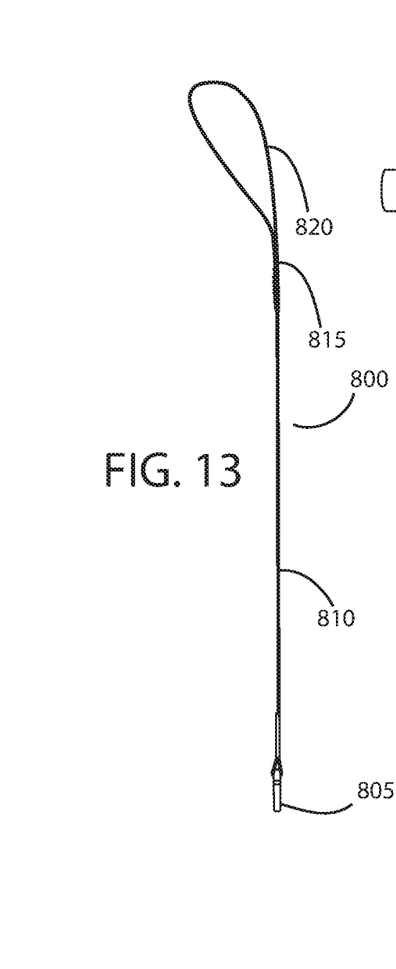
FIG. 13 is a side view of a door anchor for a traction device according to principles of the invention.

FIGS. 11 through 13 illustrate an alternative anchor 800. The anchor 800 is comprised of an elongated webbing strip 810 with a D-ring 805 or similar coupling attached at one end, a loop 820 formed at the opposite end and an area of increased thickness 815 comprised of a plurality of overlapping folded layers of webbing stitched together. The loop 820 is sized to slip over a door knob or table leg. The thickened area 815 (i.e., tab) is sufficiently thick to prevent passage between a hinged side of a door and a door frame, when the door is closed. Thus, the thickened area 815 is a substitute tab for the plastic tab 315 of the anchor embodiment of FIGS. 7 through 9. The thickened area 815 may be comprised of two, three, four or more layers of webbing stitched with a strong thread. The webbing may be flat or tubular and comprised of any synthetic material suitable for load carrying webbing, such as, but not limited to nylon, polypropylene, polyester or aramid. The stitching may be comprised of one or more strands of synthetic thread, such as, but not limited to, nylon or polyester. While a D-ring 805 is illustrated for attachment to shock cord 205, 210, other attachments such as carabiners, shackles, loops, spring clips, buckles and the like may be utilized within the scope of the invention.

The anchor strap 800 of FIGS. 11 through 13 may be used in a variety of ways. As one example, the loop 820 may be slipped over a door knob on the side of the door opposite the person using using the sling assembly 100. The webbing strip 810 extends between the door and door frame top the side of the door with the person using using the sling assembly 100. The D-ring 805 is then on the side of the door with the person using using the sling assembly 100.

Figure 14:
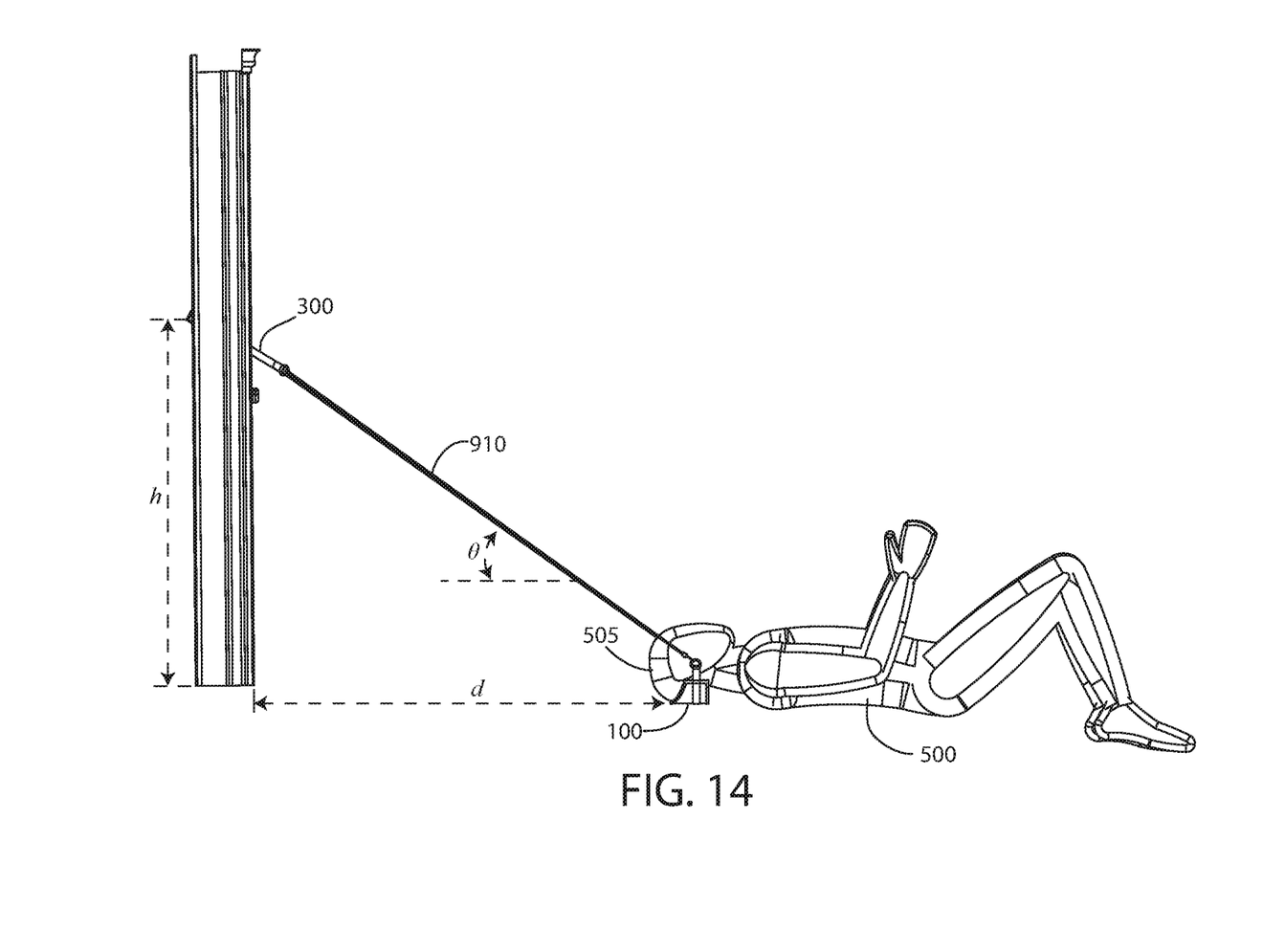
FIG. 14 is a side view that conceptually illustrates a traction device in use with a single tether (shock cord) according to principles of the invention.
Figure 15:
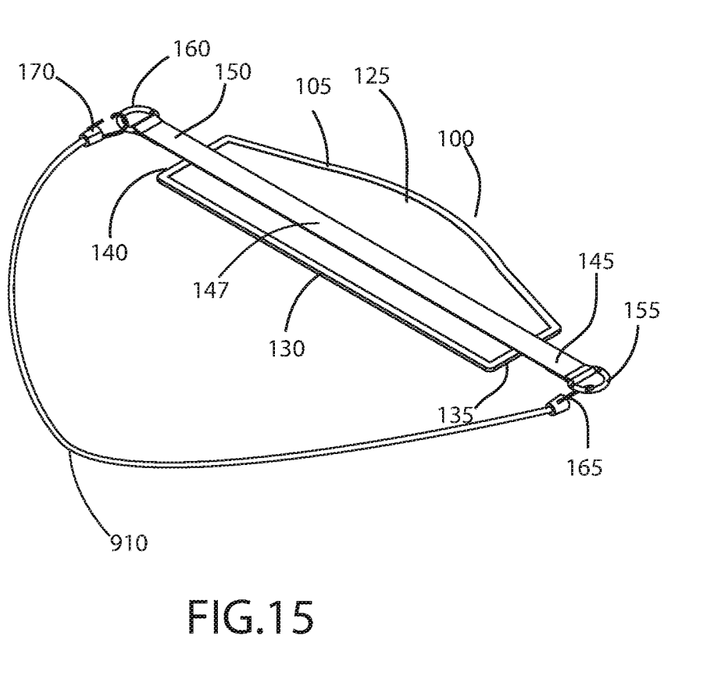
FIG. 15 is a bottom perspective view that conceptually illustrates a sling assembly for a traction device in use with a single tether (shock cord) according to principles of the invention.

FIGS. 14 and 15 illustrate an embodiment with a single shock cord (flexible elastic tether) 910. One end is attached to one side of the sling. The other end is attached to the other side of the sling. The middle of the cord 910 extends through the connector (D-ring) of the anchor 300. Thus, a single tether may be used in lieu of multiple tethers.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A portable traction device for use on a floor against a user's head, the portable traction device comprising:
    a sling, the sling being elongated and having a first side, a second side opposite the first side, a superior edge, and an inferior edge, and the sling comprising a flexible material and being sized to cradle an occipital bone portion of a user's head between the superior edge and the inferior edge of the sling during use wherein the first side extends to a first side of the user's head and the second side extends to a second side of the user's head and a frictional portion of the sling frictionally engages the occipital bone portion of the user's head;
    a pair of side attachments including a first side attachment and a second side attachment, the first side attachment extending from the first side of the sling, and the second side attachment extending from the second side of the sling;
    a pair of flexible elastic tether segments, each of the flexible elastic tether segments including a proximal end and a distal end, wherein the proximal ends of the tether segments are attached to the pair of side attachments of the sling; and
    an anchor removably attached to an anchoring object, at a height above a floor, while the portable traction device is in use, wherein the anchor comprises an anchor loop, an anchor strap, and an anchor connector, the anchor loop sized to fit over a door knob, the anchor strap disposed between and connecting the anchor loop and the anchor connector, and the anchor connector being attached to respective distal ends of each of the flexible elastic tether segments,
    wherein the flexible elastic tether segments are strained at an acute angle relative to the floor while the portable traction device is in use, the strained flexible elastic tether segments producing a tensile force including a first vector component parallel to the floor and towards the anchor and a second vector component perpendicular to the floor and upward.

2. The portable traction device of claim 1, the superior edge of the sling being arcuate.

3. The portable traction device of claim 1, further comprising at least one cushion, the at least one cushion including a base cushion attached to the sling between the superior edge and the inferior edge and approximately centered between the first side of the sling and the second side of the sling.

4. The portable traction device of claim 3, further including a first side cushion disposed between the base cushion and the first side of the sling and a second side cushion disposed between the base cushion and the second side of the sling.

5. The portable traction device of claim 1, the sling comprising a first layer, a second layer, and a third layer, wherein the first layer and the third layer comprise flexible fabric and the second layer comprises a flexible cushioning material disposed between the first layer and the third layer.

6. The portable traction device of claim 1, the sling including a back side and a front side opposite the back side, the front side of the sling contacting a user's head when in use, and the traction device further comprising a strap, the strap extending from the first side attachment across the back side of the sling to the second side attachment, the strap extending beyond the first side of the sling and the second side of the sling, and the strap being attached to the back side of the sling.

7. The portable traction device of claim 1, each of the pair of side attachments comprising one of a shackle, ring, hook and clip.

8. The portable traction device of claim 1, each of the pair of flexible elastic tether segments comprising a shock cord.

9. The portable traction device of claim 1, the proximal end of each of the pair of flexible elastic tether segments including a first connector, and the distal end of each of the pair of flexible elastic tether segments including a second connector.

10. The portable traction device of claim 9, the first connector comprising one of a hook, carabiner, and shackle, and the second connector comprising one of a hook, carabiner, and shackle.

11. The portable traction device of claim 1, wherein the anchor comprises an anchor tab having a tab thickness greater than a thickness of the strap, and wherein the anchor tab comprises a structure selected from the group consisting of: a plastic tab and a plurality of overlaying layers of webbing stitched together.

12. A portable traction device for use on a floor against a user's head, the portable traction device comprising:
    a sling, the sling being elongated and having a first side, a second side opposite the first side, a superior edge, and an inferior edge, the sling comprising a flexible material and being sized to cradle an occipital bone portion of a user's head between the superior edge and the inferior edge of the sling while the first side extends to a first side of the user's head and the second side extends to a second side of the user's head, and the sling including a frictional portion that frictionally engages the occipital bone portion of the user's head;

a pair of side attachments including a first side attachment and a second side attachment, the first side attachment extending from the first side of the sling, and the second side attachment extending from the second side of the sling; and a flexible elastic tether including a first end and a second end, the first end of the flexible elastic tether attached to the first side attachment of the sling, and the second end of the flexible elastic tether attached to the second side attachment of the sling;

an anchor removably attached to an anchoring object, at a height above a floor, while the portable traction device is in use, the anchor including an anchor connector, the flexible elastic tether extending through the anchor connector; and the flexible elastic tether being strained at an acute angle relative to the floor, while the portable traction device is in use, the strained flexible elastic tether producing a tensile force including a first vector component parallel to the floor and towards the anchor and a second vector component perpendicular to the floor and upward.

13. The portable traction device of claim 12, the sling including a back side and a front side opposite the back side, the front side of the sling contacting a user's head when in use, and the traction device further comprising a strap, the strap extending from the first side attachment across the back side of the sling to the second side attachment, the strap extending beyond the first side of the sling and the second side of the sling, and the strap being attached to the back side of the sling.

14. The portable traction device of claim 13, each of the pair of side attachments comprising one of a shackle, ring, hook and clip.

15. The portable traction device of claim 14, the flexible elastic tether comprising a shock cord.

16. The portable traction device of claim 15, the first end of the flexible elastic tether including a first connector, and the second end of the flexible elastic tether including a second connector, and the first connector comprising one of a hook, carabiner, and shackle, and the second connector comprising one of a hook, carabiner, and shackle.

17. The portable traction device of claim 16, the anchor comprising an anchor tab, an anchor strap, and an anchor connector, the anchor strap disposed between and connecting the anchor tab and the anchor connector, and the anchor connector being attached to each distal end of each of the pair of flexible elastic tethers.

18. A method of applying cervical traction to a user comprising steps of:

providing the portable traction device of claim 12;

stretching the flexible elastic tether at an acute angle relative to the floor to produce the tensile force including the first vector component parallel to the floor and towards the anchor, and the second vector component perpendicular to the floor and upward;

cradling, with the sling while the at least one flexible elastic tether is stretched, the head of the user, the user being substantially supine on a floor with the user's head spaced apart from and aimed towards the anchoring object and the user's feet aimed away from the anchoring object.

19. A portable traction device for providing cervical traction to a user in a supine position, the portable traction device comprising:

a sling defined by a first side, a second side opposite the first side, a superior edge, and an inferior edge opposite the superior edge and adjacent to each of the first and second sides, the sling comprising a frictional portion configured to frictionally engage the occipital bone portion of a user's head during use;

a flexible elastic tether having a first end associated with the first side of the sling and a second end associated with the second side of the sling;

an anchor comprising an anchor tab and an anchor connector associated with the anchor tab, the anchor tab being configured to selectively secure the anchor to an anchoring object, wherein the flexible elastic tether is configured to extend through the anchor connector and associate the sling with the anchor via the flexible elastic tether, and wherein the flexible elastic tether is strained and at an acute angle relative to the floor while the portable traction device is in use, the strained flexible elastic tether producing a tensile force including a vector component parallel to the floor towards the anchor and a vector component perpendicular to the floor and upward.

* * * * *